United States Patent
Suchanek

(10) Patent No.: US 10,512,894 B2
(45) Date of Patent: *Dec. 24, 2019

(54) POROUS BODIES WITH ENHANCED PORE ARCHITECTURE

(71) Applicant: Scientific Design Company, Inc., Little Ferry, NJ (US)

(72) Inventor: Wojciech L. Suchanek, Wyckoff, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/722,696

(22) Filed: Oct. 2, 2017

(65) Prior Publication Data

US 2018/0021755 A1    Jan. 25, 2018

Related U.S. Application Data

(63) Continuation of application No. 15/171,278, filed on Jun. 2, 2016, now Pat. No. 9,776,169.

(Continued)

(51) Int. Cl.
*B01J 21/04* (2006.01)
*C04B 38/00* (2006.01)
(Continued)

(52) U.S. Cl.
CPC ........... *B01J 21/04* (2013.01); *B01J 19/0013* (2013.01); *B01J 23/04* (2013.01); *B01J 23/36* (2013.01);
(Continued)

(58) Field of Classification Search
CPC ...... B01J 21/04; C04B 38/00; C04B 38/0096; C04B 38/08; C04B 41/009; C04B 41/4535; C04B 41/5116; C04B 41/88
See application file for complete search history.

(56) References Cited

U.S. PATENT DOCUMENTS 3,563,914 A    2/1971  Wattimena
3,702,259 A    11/1972 Nielsen
(Continued)

FOREIGN PATENT DOCUMENTS

CN    1646219 A    7/2005
CN    101237926 A   8/2008
(Continued)

OTHER PUBLICATIONS

C. Falamaki, et al., "Dual behavior of CaCO3 as a porosifier and sintering aid in the manufacture of alumina membrane/catalyst supports", Journal of the European Ceramic Society 24, accepted Oct. 25, 2003, pp. 3195-3201.

(Continued)

*Primary Examiner* — Cam N. Nguyen
(74) *Attorney, Agent, or Firm* — Scully Scott Murphy and Presser

(57) ABSTRACT

A porous body is provided with enhanced fluid transport properties that is capable of performing or facilitating separations, or performing reactions and/or providing areas for such separations or reactions to take place. The porous body includes at least 80 percent alpha alumina and has a pore volume from 0.3 mL/g to 1.2 mL/g and a surface area from 0.3 m$^2$/g to 3.0 m$^2$/g. The porous body further includes a pore architecture that provides at least one of a tortuosity of 7.0 or less, a constriction of 4.0 or less and a permeability of 30 mdarcys or greater. The porous body can be used in a wide variety of applications such as, for example, as a filter, as a membrane or as a catalyst carrier.

14 Claims, 8 Drawing Sheets

Related U.S. Application Data

(60) Provisional application No. 62/169,706, filed on Jun. 2, 2015, provisional application No. 62/169,766, filed on Jun. 2, 2015.

(51) Int. Cl.

| | | |
|---|---|---|
| *C04B 38/08* | (2006.01) | |
| *C04B 41/00* | (2006.01) | |
| *C04B 41/45* | (2006.01) | |
| *C04B 41/51* | (2006.01) | |
| *C04B 41/88* | (2006.01) | |
| *B01J 35/10* | (2006.01) | |
| *C07D 301/22* | (2006.01) | |
| *B01J 35/04* | (2006.01) | |
| *B01J 37/00* | (2006.01) | |
| *B01J 37/08* | (2006.01) | |
| *B01J 23/50* | (2006.01) | |
| *C07D 301/10* | (2006.01) | |
| *B01J 19/00* | (2006.01) | |
| *B01J 23/04* | (2006.01) | |
| *B01J 23/36* | (2006.01) | |
| *C04B 111/00* | (2006.01) | |

(52) U.S. Cl.
CPC ............... *B01J 23/50* (2013.01); *B01J 35/04* (2013.01); *B01J 35/108* (2013.01); *B01J 35/1009* (2013.01); *B01J 35/1038* (2013.01); *B01J 35/1042* (2013.01); *B01J 35/1047* (2013.01); *B01J 37/0018* (2013.01); *B01J 37/086* (2013.01); *C04B 38/00* (2013.01); *C04B 38/0096* (2013.01); *C04B 38/08* (2013.01); *C04B 41/009* (2013.01); *C04B 41/4535* (2013.01); *C04B 41/5116* (2013.01); *C04B 41/88* (2013.01); *C07D 301/10* (2013.01); *C07D 301/22* (2013.01); *B01J 2219/00051* (2013.01); *C04B 2111/0081* (2013.01)

(56) References Cited

U.S. PATENT DOCUMENTS

| | | | |
|---|---|---|---|
| 4,410,453 | A | 10/1983 | Kiovsky et al. |
| 4,419,276 | A | 12/1983 | Bhasin et al. |
| 4,761,394 | A | 8/1988 | Lauritzen |
| 4,766,105 | A | 8/1988 | Lauritzen |
| 4,874,879 | A | 10/1989 | Lauritzen et al. |
| 4,908,343 | A | 3/1990 | Bhasin |
| 5,011,807 | A | 4/1991 | Hayden et al. |
| 5,057,481 | A | 10/1991 | Bhasin |
| 5,099,041 | A | 3/1992 | Hayden et al. |
| 5,102,848 | A | 4/1992 | Soo et al. |
| 5,112,795 | A | 5/1992 | Minahan et al. |
| 5,155,242 | A | 10/1992 | Shankar et al. |
| 5,187,140 | A | 2/1993 | Thorsteinson et al. |
| 5,380,885 | A | 1/1995 | Kemp |
| 5,384,302 | A | 1/1995 | Gerdes et al. |
| 5,407,888 | A | 4/1995 | Herzog et al. |
| 5,597,773 | A | 1/1997 | Evans et al. |
| 5,663,385 | A | 9/1997 | Kemp |
| 5,703,253 | A | 12/1997 | Evans et al. |
| 5,801,259 | A | 9/1998 | Kowaleski |
| 6,562,749 | B1 | 5/2003 | Lednor et al. |
| 7,102,022 | B2 | 9/2006 | Evans et al. |
| 7,439,375 | B2 | 10/2008 | Lockemeyer |
| 7,485,597 | B2 | 2/2009 | Lockemeyer et al. |
| 7,560,577 | B2 | 7/2009 | Hirota et al. |
| 7,714,152 | B2 | 5/2010 | Pak |
| 8,008,515 | B2 | 8/2011 | Shima et al. |
| 8,017,546 | B2 | 9/2011 | Shima et al. |
| 8,084,390 | B2 | 12/2011 | Gerdes et al. |
| 8,357,813 | B2 | 1/2013 | Gerdes et al. |
| 8,456,294 | B2 | 6/2013 | Emigh et al. |
| 8,546,294 | B2 | 10/2013 | Liu et al. |
| 8,685,883 | B2 | 4/2014 | Bryden et al. |
| 8,716,504 | B2 | 5/2014 | Liu et al. |
| 8,871,677 | B2 | 10/2014 | Richard et al. |
| 8,895,469 | B2 | 11/2014 | Chen et al. |
| 8,937,031 | B2 | 1/2015 | Lockemeyer et al. |
| 8,987,483 | B2 | 3/2015 | Basrur et al. |
| 9,073,035 | B2 | 7/2015 | Richard et al. |
| 9,339,798 | B2 | 5/2016 | Richard et al. |
| 9,776,169 | B2 | 10/2017 | Suchanek |
| 10,040,055 | B2 | 8/2018 | Verrier et al. |
| 10,124,318 | B2 * | 11/2018 | Suchanek ................ B01J 23/50 |
| 2005/0096219 | A1 | 5/2005 | Szymanski et al. |
| 2008/0138569 | A1 | 6/2008 | Collier et al. |
| 2009/0082584 | A1 | 3/2009 | Rizkalla et al. |
| 2009/0227820 | A1 | 9/2009 | Pak et al. |
| 2010/0056816 | A1 | 3/2010 | Wallin et al. |
| 2010/0267973 | A1 | 10/2010 | Liu et al. |
| 2012/0022277 | A1 | 1/2012 | Hashimoto et al. |
| 2012/0065055 | A1 | 3/2012 | Jiang et al. |
| 2012/0108832 | A1 | 5/2012 | Chen et al. |
| 2012/0323026 | A1 | 12/2012 | Lockemeyer et al. |
| 2013/0231493 | A1 | 9/2013 | Shishkov et al. |
| 2014/0100379 | A1 | 4/2014 | Richard et al. |
| 2014/0187807 | A1 | 7/2014 | Pak et al. |
| 2015/0209774 | A1 | 7/2015 | Richard et al. |
| 2015/0343433 | A1 | 12/2015 | Dobner et al. |
| 2016/0354759 | A1 | 12/2016 | Suchanek et al. |
| 2016/0354760 | A1 | 12/2016 | Suchanek |
| 2018/0021755 | A1 | 1/2018 | Suchanek |

FOREIGN PATENT DOCUMENTS

| | | |
|---|---|---|
| EP | 0327356 A1 | 8/1989 |
| GB | 1422451 | 1/1976 |
| WO | 9623585 A1 | 8/1996 |
| WO | 2004002954 A2 | 1/2004 |
| WO | 2010008919 A2 | 1/2010 |
| WO | 2014189741 A2 | 11/2014 |

OTHER PUBLICATIONS

International Search Report dated Sep. 13, 2016 received in corresponding foreign application.
International Search Report dated Sep. 19, 2016 received in corresponding foreign application.
Brunauer, S., et al., "Adsorption of Gases in Multimolecular Layers", J. Am. Chem. Soc., Feb. 1938, pp. 309-316.
Green, D. W., et al., "Perry's Engineering Handbook", 8th Edition, 2007, p. 5-58, McGraw-Hill.
Ghanbarian, B., et al., "Tortuosity in Porous Media: A Critical Review", Soil Science Society of America Journal, Sep. 20, 2013, pp. 1461-1477, 77.
"C Computing Algorithm for Volumetric Pressure Coefficients of Compressibility", AutoPore V Operator Manual, Micromeritics, Jun. 2014, 18 pages, Version: 1.01.
Lowell, S., et al., "Characterization of Porous Solids and Powders: Surface Area, Pore Size and Density", Springer 2006, pp. 200-203.
European Office Action dated May 27, 2019, received in a related foreign application No. 16804376.8.
European Office Action dated May 28, 2019, received in a related foreign application No. 16804377.6.

* cited by examiner

POROUS BODIES WITH ENHANCED PORE ARCHITECTURE

CROSS REFERENCE TO RELATED APPLICATIONS

This application is a continuation of U.S. patent application Ser. No. 15/171,278, filed Jun. 2, 2016, now U.S. Pat. No. 9,776,169 issued on Oct. 3, 2017, which claims the benefit of U.S. Provisional Patent Application Nos. 62/169,706 and 62/169,766 filed Jun. 2, 2015, the entire content and disclosure of each are incorporated herein by reference.

FIELD OF THE INVENTION

The present invention relates to porous bodies and more particularly to porous bodies that can be used in a wide variety of applications including, for example, as a filter, a membrane, or a catalyst carrier.

BACKGROUND

In the chemical industry and the chemical engineering industry, reliance is oftentimes made on using porous bodies, including porous ceramic bodies, which are capable of performing or facilitating separations or reactions and/or providing areas for such separations and reactions to take place. Examples of separations or reactions include: filtration of gases and liquids, adsorption, reverse osmosis, dialysis, ultrafiltration, or heterogeneous catalysis. Although the desired physical and chemical properties of such porous bodies vary depending on the particular application, there are certain properties that are generally desirable in such porous bodies regardless of the final application in which they will be utilized.

For example, porous bodies may be substantially inert so that the porous bodies themselves do not participate in the separations or reactions taking place around, on or through them in a way that is undesired, unintended, or detrimental. In applications where it is desired to have the components that are being reacted or separated pass through, or diffuse into, the porous body, a low diffusion resistance (e.g., high effective diffusivity) would be advantageous.

In some applications, the porous bodies are provided within a reaction or separation space, and so they are desirably of high pore volume and/or high surface area, in order to improve the loading and dispersion of the desired reactants, and also to provide enhanced surface area on which the reactions or separations can take place. These applications also require sufficient mechanical integrity to avoid being damaged, i.e., crushed, chipped or cracked, during transport or placement. However, the combination of high mechanical strength with high pore volume in a porous body is not easy to achieve because the strength decreases exponentially with increasing porosity.

In view of the above, there is a need for providing porous bodies that have a pore architecture that has enhanced fluid transport properties, particularly gas diffusion properties, as well as high mechanical integrity.

SUMMARY

A porous body is provided that is capable of performing or facilitating separations, or performing reactions and/or providing areas for such separations or reactions to take place. In one embodiment of the present invention, the porous body includes at least 80 percent alpha alumina and has a pore volume from 0.3 mL/g to 1.2 mL/g and a surface area from 0.3 m$^2$/g to 3.0 m$^2$/g. The porous body further includes a pore architecture that provides at least one of a tortuosity of 7 or less, a constriction of 4 or less and a permeability of 30 mdarcys or greater.

The porous body of the present invention can be used in a wide variety of applications such as, for example, as a filter, as a membrane or as a catalyst carrier. In one example, the porous body of the present invention is used as a carrier for a silver-based epoxidation catalyst. In such an embodiment, the silver-based epoxidation catalyst includes a carrier comprising at least 80 percent alpha alumina and having a pore volume from 0.3 mL/g to 1.2 mL/g, a surface area from 0.3 m$^2$/g to 3.0 m$^2$/g, and a pore architecture that provides at least one of a tortuosity of 7 or less, a constriction of 4 or less and a permeability of 30 mdarcys or greater. The catalyst further includes a catalytic amount of silver disposed on and/or in the carrier, and a promoting amount of one or more promoters disposed on and/or in the carrier.

DETAILED DESCRIPTION

The present invention will now be described in greater detail by referring to the following discussion and drawings that accompany the present invention. In the following description, numerous specific details are set forth, such as particular structures, components, materials, dimensions, processing steps and techniques, in order to provide an understanding of the various embodiments of the present invention. However, it will be appreciated by one of ordinary skill in the art that the various embodiments of the present invention may be practiced without these specific details. As used throughout the present invention, the term "about" generally indicates no more than ±10%, ±5%, ±2%, ±1% or ±0.5% from a number.

Typical representations of porous body microstructures, e.g., catalyst carriers for epoxidation of olefins, include the following measurable features and variety of their combinations: (1) Pore size distribution represented either as cumulative intrusion curves or as log differential size distributions, (2) Ranges of pore sizes with assigned specific pore volumes or pore volume fractions of total materials pore volumes, (3) BET surface area (4) Total pore volume, (5) Morphology of crystallites constituting the ceramic microstructure, such as platelets or fibers, and (6) Purity of the support expressed either as total purity or surface purity.

The Applicant of the present invention has determined that the above approach to characterize porous bodies is not a reliable way to properly characterize the pore architecture of such porous bodies because pore size distributions or ranges of pore sizes with assigned specific pore volumes are insufficient to properly characterize porous microstructures. In other words, exactly the same cumulative curves and their derivatives, such as log differential pore size distribution can represent completely different microstructures.

Figure 1A:
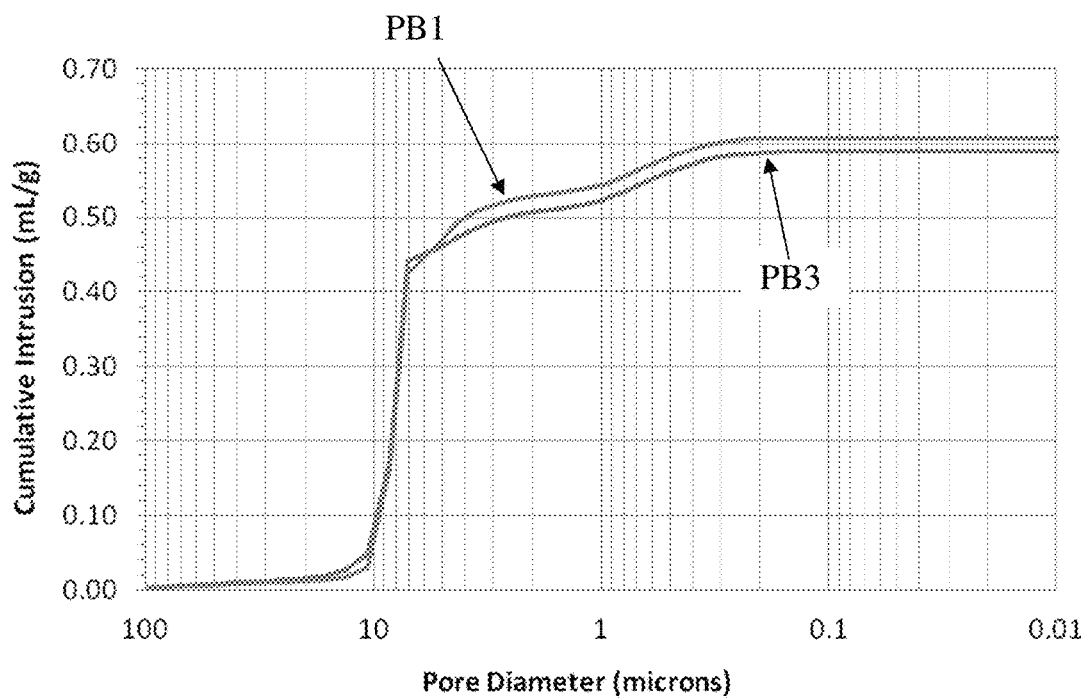
FIG. 1A shows the cumulative intrusion curves of porous body 1 (PB1) and porous body 3 (PB3).
Figure 1B:
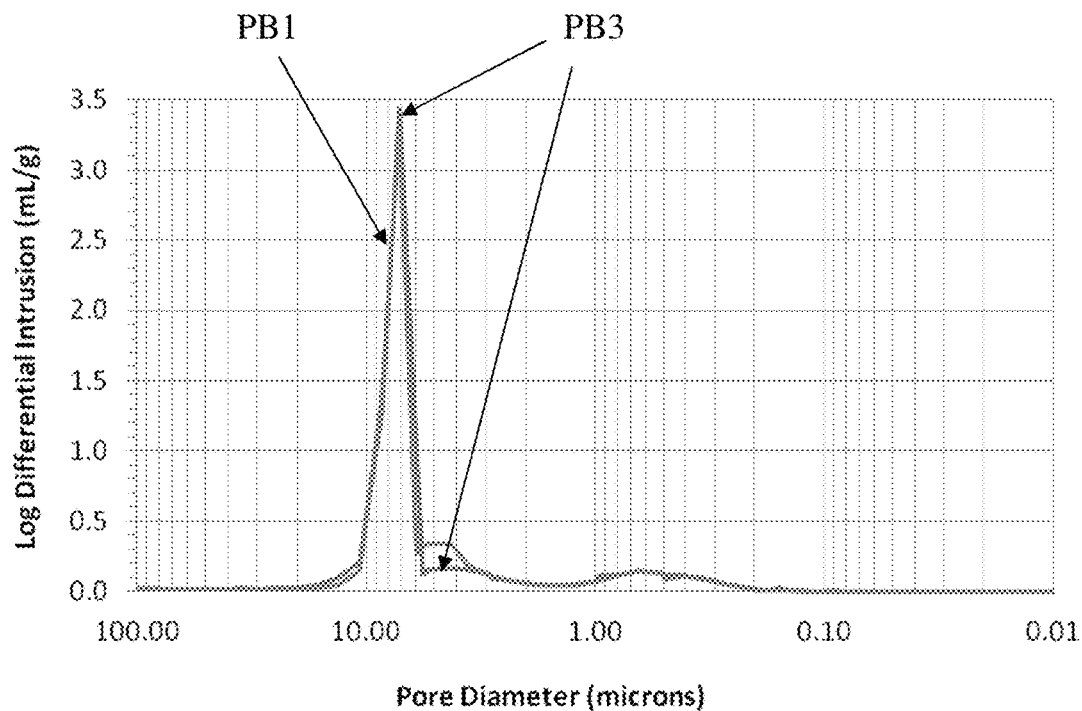
FIG. 1B shows the log differential intrusion curves of PB1 and PB3.
Figure 2A:
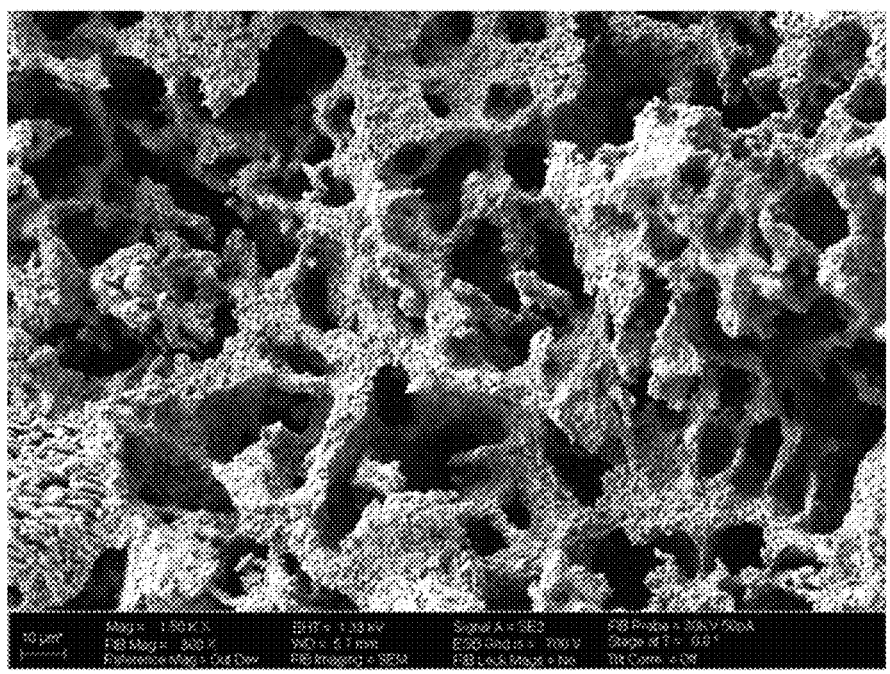
FIGS. 2A-2B are SEM images of PB1 at magnifications of 1500× (FIG. 2A) and 5000× (FIG. 2B).
Figure 2B:
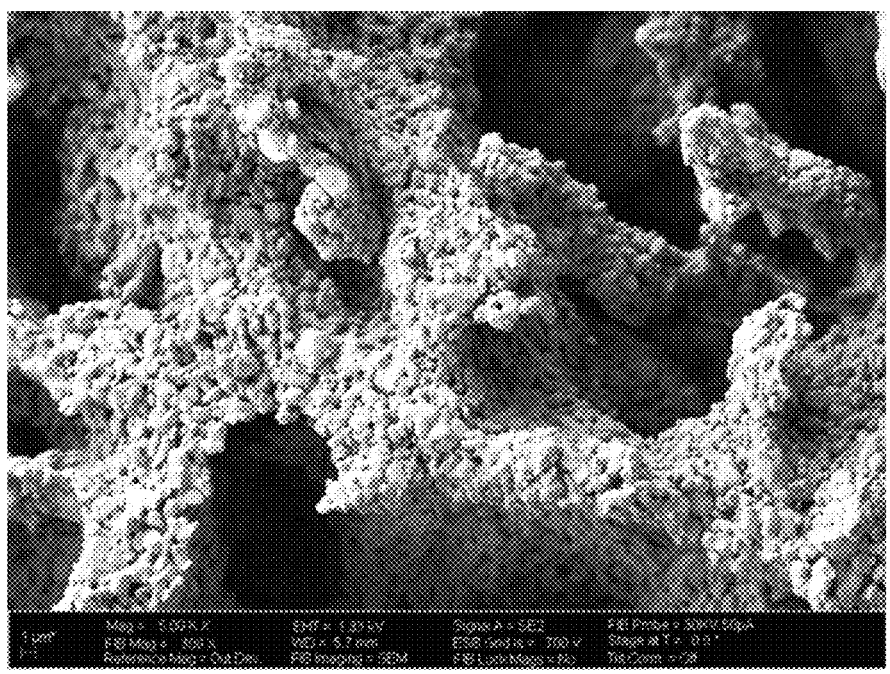
Figure 3A:
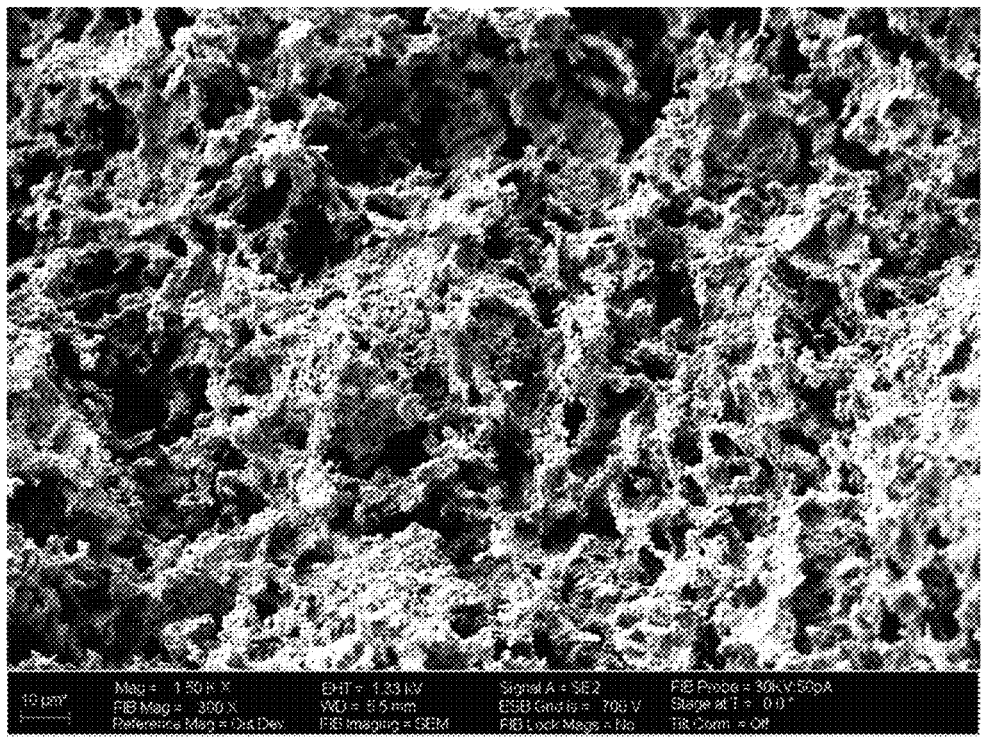
FIGS. 3A-3B are SEM images of PB3 at magnifications of 1500× (FIG. 3A) and 5000× (FIG. 3B).
Figure 3B:
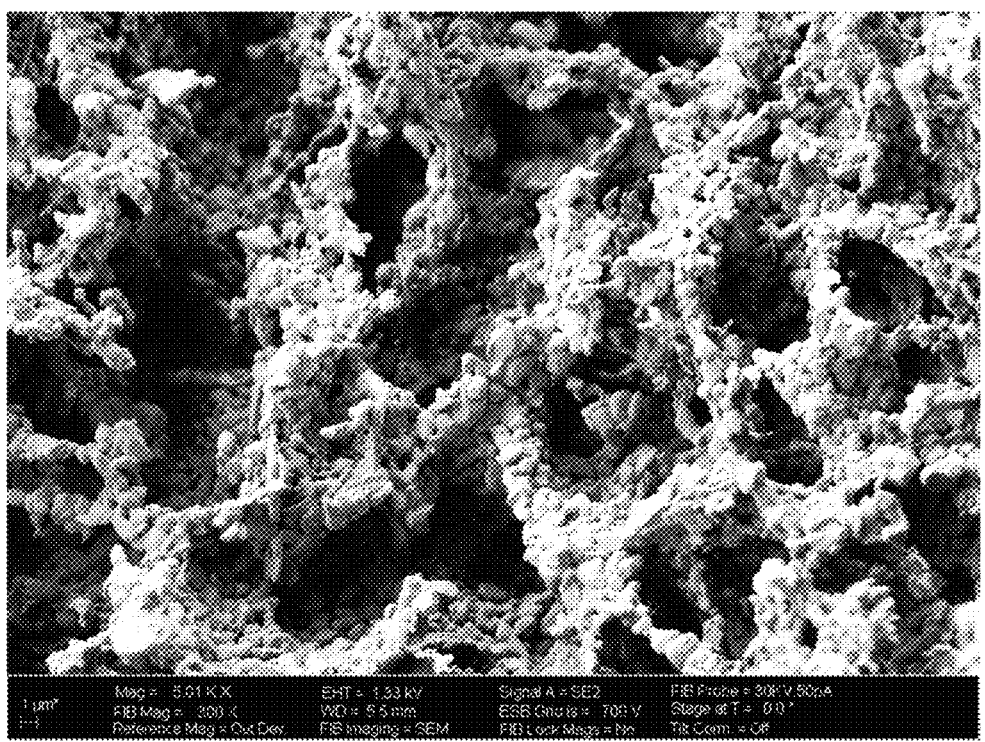

The above is demonstrated in FIGS. 1A, 1B, 2A, 2B, 3A, and 3B. Notably, FIG. 1A shows the cumulative intrusion curves, while FIG. 1B shows the log differential intrusion curves, measured on porous body 1 (PB1) and porous body 3 (PB3) by Hg intrusion porosimetry; PB1 and PB3 are inventive porous bodies which are described in greater detail in Example 1. Both types of curves are overlapping within the accuracy of the measurement, i.e., ±0.01 mL/g. The prior art teaches that both curves should represent the same porous architectures that result in particular performance of the porous ceramics. However, PB1 and PB3 have very different porous architectures and other properties, as shown in FIGS. 2A, 2B, 3A, and 3B, and in Table 2. PB1 consists of a smaller number of larger pores separated by thick walls, has a higher tortuosity and constriction, and thus lower effective diffusivity than PB3. Conversely, PB3 consists of a larger number of smaller pores separated by thin walls, and has a lower tortuosity and constriction, and higher effective diffusivity than PB1.

In order to properly characterize porous bodies for applications in filters, membranes, or catalyst carriers, pore architecture and consequently fluid transport-related properties must also be determined.

Among very important parameters in determining the diffusive gas transport through a porous body are tortuosity and constriction. Tortuosity is determined by the ratio of the real length of flow path through a porous body to the shortest distance across that porous body [see, for example, B. Ghanbarian et al., Soil Sci. Soc. Am. J., 77, 1461-1477 (2013)]. Constriction is a function of the area ratio of large pores to small pores. Thus, lowering the values of tortuosity and/or constriction enhances the diffusive transport through a porous material, i.e., increases the effective diffusivity, which is very important for instance in catalytic applications.

If there is a pressure drop across the porous body, permeability becomes important. Permeability indicates ability of fluids to flow through porous bodies and can be described by the Darcy's law shown in Equation 1, where V is fluid flow velocity, k is permeability, $\mu$ is dynamic viscosity of the fluid, $\Delta P$ is pressure difference across porous body with thickness of $\Delta x$:

$$V = \frac{k}{\mu} \frac{\Delta P}{\Delta x} \quad \text{(Eq. 1)}$$

Thus higher values of permeability will enhance the pressure-driven fluid flow across a porous body, which is important in such applications as sorption, filtration, or catalysis.

Surprisingly, the aforementioned fluid transport-determining properties of porous bodies cannot be found in the literature to characterize porous architectures, particularly as-related to catalyst carriers for epoxidation of olefins. Moreover, there has been no indication in the literature of the necessary values of tortuosity, constriction or permeability which provide a pore architecture to a porous body that can achieve enhanced properties, especially in regard to catalyst performance. The present invention provides porous bodies that have a pore architecture that has enhanced fluid transport properties, in particular effective gas diffusivity, and high mechanical integrity.

Unless otherwise specified the following methodology of measurements were employed in the present application:

Cumulative intrusion curves and Log differential intrusion curves were acquired for representative samples of the porous bodies by mercury (Hg) intrusion porosimetry, principles of which are described in Lowell et al., *Characterization of Porous Solids and Powders: Surface Area, Pore Size and Density*, Springer, 2006. The equipment used was AutoPore IV 9500 Series porosimeter from Micromeritics Instruments Co., Norcross, Ga. The Hg intrusion pressure ranged between 1.5 and 60,000 psi, which corresponds to pore sizes between 140 microns and 3.6 nm. The following Hg parameters were used for calculations: surface tension of 480 dynes/cm, density of 13.53 g/mL, and contact angle of 140°.

Pore volumes for the porous bodies were measured from the Hg intrusion data, which were consistent with the water absorption measurements.

In the present invention, water absorption of the porous bodies was measured by placing a 10 g representative sample of a porous body into a flask, which was then evacuated to about 0.1 torr for 5 min. Subsequently, deionized water was aspirated into the evacuated flask to cover the porous bodies while maintaining the pressure at about 0.1 torr. The vacuum was released after about 5 minutes to restore ambient pressure, hastening complete penetration of water into the pores. Subsequently, the excess water was drained from the impregnated sample. Water absorption was calculated by dividing total water weight in the pores (i.e., wet mass-dry mass of the sample) by the weight of the dry sample at room temperature.

Additional pore architecture parameters of the porous bodies such as tortuosity, constriction, and permeability, were also calculated from the Hg intrusion data, as described below.

The tortuosity, $\xi$, was calculated from Equation 2, where $D_{avg}$ is weighted average pore size, k is permeability, $\rho$ is true materials density, and $I_{tot}$ is total specific intrusion volume [See, *AutoPore V Operator Manual*, Micromeritics, 2014]:

$$\xi = \sqrt{\frac{D_{avg}^2}{4 \cdot 24k(1 - \rho I_{tot})}} \quad \text{(Eq. 2)}$$

The constriction, $\sigma$, was calculated from Equation 3, where $\xi$ is tortuosity and $\tau$ is tortuosity factor, calculated from the Carnigilia equation [See, *AutoPore V Operator Manual*, Micromeritics, 2014]:

$$\sigma = \frac{\xi}{\tau} \quad \text{(Eq. 3)}$$

The permeability, as defined by the Darcy's law (Eq. 1, above), can be calculated by combining Darcy's and Poiseuille'd equations [See, for example, Lowell et al., *Characterization of Porous Solids and Powders*, Springer, 2006]. For an arbitrary pore shape factor, f, the permeability k is expressed by Equation 4, where τ is tortuosity factor, P is materials porosity, and d is pore diameter:

$$k = \frac{P^3 d^2}{16 f \tau (1-P)^2} \quad \text{(Eq. 4)}$$

Once tortuosity and pore volumes have been measured, effective diffusivity can be calculated from Equation 5, where P is materials porosity, D is diffusivity, $D_{eff}$ is effective diffusivity, and ξ is tortuosity [D. W. Green, R. H. Perry, *Perry's Engineering Handbook*, 8$^{th}$ Edition, McGraw-Hill, 2007]

$$D_{eff} = \frac{PD}{\xi} \quad \text{(Eq. 5)}$$

In order to calculate absolute values of effective diffusivity, $D_{eff}$ in a porous solid, absolute values of gas diffusivity, D, must be known per Eq. 5, in addition to the material porosity and tortuosity. However, in order to compare effective diffusivity properties of different porous solids (e.g., inventive examples of the present invention), it is possible to calculate relative numbers of effective diffusivity normalized to a standard material (comparative example of the present invention). With the assumption that gas diffusivity, D, is the same in all cases, it requires only knowledge of porosity and tortuosity of the porous materials (see Equation 6).

$$\frac{D_{eff,1}}{D_{eff,0}} = \frac{P_1}{\xi_1} \frac{\xi_0}{P_0} \quad \text{(Eq. 6)}$$

Total porosity is defined as the void volume divided by the total volume of the sample. It can be calculated from mercury porosimetry or water absorption, using theoretical density of the carrier material.

Specific surface areas of the porous bodies were determined by nitrogen adsorption using the B.E.T. method, details of which are described in Brunauer, S., Emmett, P. H. and Teller, *J. Am. Chem. Soc.*, 60, 309-16 (1938).

The flat plate crush strength of the porous bodies was measured using a standard test method for single pellet crush strength of formed catalysts and catalyst carriers, ASTM Standard ASTM D4179.

Attrition measurements of the porous bodies were performed using a standard test method for attrition and abrasion of catalysts and catalyst carriers, ASTM Standard ASTM D4058.

Scanning electron microscopy (SEM) was used to characterize pore architectures of the porous bodies of the present invention. The SEM photographs were acquired using Zeiss Auriga small Dual-Beam FIB-SEM. Pellets of each porous body were investigated on the cross-section (fracture surface) at 1.33 kV with about 5 mm working distance. No conductive coatings were sputtered on the samples.

As stated above, the present invention provides a porous body that has a pore architecture that has enhanced fluid transport properties and high mechanical integrity. The porous body of the present invention may be referred to as a porous ceramic body since it contains mainly alpha alumina particles. Typically, the porous body of the present invention comprises at least 80 percent alpha alumina; the remainder being other oxides and/or non oxides and incidental impurities. More typically, the porous body of the present invention comprises from 85 percent alpha alumina to 99 percent alpha alumina, the remainder being other oxides and/or non oxides and incidental impurities.

The porous body of the present invention typically has a pore volume from 0.3 mL/g to 1.2 mL/g. More typically, the porous body of the present invention has a pore volume from 0.35 mL/g to 0.9 mL/g. In some embodiments of the present invention, the porous body of the present invention has a water absorption from 30 percent to 120 percent, with a range from 35 percent to 90 percent being more typical.

The porous body of the present invention typically has a surface area from 0.3 m$^2$/g to 3.0 m$^2$/g. In one embodiment, the porous body of the present invention has a surface area from 0.5 m$^2$/g to 1.2 m$^2$/g. In another embodiment of the present invention has a surface area above 1.2 m$^2$/g up to, and including, 3.0 m$^2$/g.

The porous body of the present invention can be monomodal or multimodal such as, for example, bimodal. The porous body of the present invention has a pore size distribution with at least one mode of pores in the range from 0.01 micrometers to 100 micrometers. In one embodiment of the present invention, at least 90 percent of the pore volume of the porous body is attributed to pores having a pore size of 20 microns or less. In yet another embodiment of the present invention, at least 85 percent of the pore volume of the porous body is attributed to pores having a size from 1 micron to 6 microns. In yet a further embodiment of the present invention, less than 15, preferably less than 10, percent of the pore volume of the porous body is attributed to pores having a size of less than 1 micron. In still a further embodiment of the present invention, at least 80 percent of the pore volume of the porous body is attributed to pores having a size from 1 micron to 10 microns. In a particular aspect of the present invention, there are essentially no pores smaller than 1 micron.

In one embodiment, the porous body of the present invention may be bimodal having a first set of pores from 0.01 microns to 1 micron and a second set of pores from greater than 1 micron to 10 microns. In such an embodiment, the first set of pores may constitute less than 15 percent of the total pore volume of the porous body, while the second set of pores may constitute more than 85 percent of the total pore volume of the porous body. In yet another embodiment, the first set of pores may constitute less than 10 percent of the total pore volume of the porous body, while the second set of pores may constitute more than 90 percent of the total pore volume of the porous body.

The porous body of the present invention typically has a total porosity that is from 55 percent to 83 percent. More typically, the porous body of the present invention has a total porosity that is from 58 percent to 78 percent.

The porous body of the present invention typically has an average flat plate crush strength from 10 N to 150 N. More typically, the porous body of the present invention has an average flat plate crush strength from 40 N to 105 N. In some embodiments, the porous body of the present invention can have an attrition value that is less than 40%, preferably less than 25%. In some embodiments of the present invention, the porous body can have attrition less that 10%.

In some embodiments of the present invention, the porous body has an initial low alkali metal content. By "low alkali metal content" it is meant that the porous body contains from 2000 ppm or less, typically from 30 ppm to 300 ppm, of alkali metal therein. Porous bodies containing low alkali metal content can be obtained by adding substantially no alkali metal during the porous body manufacturing process. By "substantially no alkali metal" it is meant that only trace amounts of alkali metal are used during the porous body manufacture process as impurities from other constituents of the porous body. In another embodiment, a porous body having a low alkali metal content can be obtained by performing various washing steps to the porous body precursor materials used in forming the porous body. The washing steps can include washing in a base, an acid, water, or another solvent.

In other embodiments of the present invention, the porous body has an alkali metal content that is above the value mentioned above for the porous body having substantially no alkali metal content. In such an embodiment the porous body typically contains a measurable level of sodium on the surface thereof. The concentration of sodium at the surface of the carrier will vary depending on the level of sodium within the different components of the porous body as well as the details of its calcination. In one embodiment of the present invention, the porous body has a surface sodium content of from 2 ppm to 150 ppm, relative to the total mass of the porous body. In another embodiment of the present invention, the porous body has a surface sodium content of from 5 ppm to 70 ppm, relative to the total mass of the carrier. The sodium content mentioned above represents that which is found at the surface of the carrier and that which can be leached, i.e., removed, by nitric acid (hereafter referred to as acid-leachable sodium).

The quantity of acid leachable sodium present in the porous bodies of the present invention can be extracted from the catalyst or carrier with 10% nitric acid in deionized water at 100° C. The extraction method involves extracting a 10-gram sample of the catalyst or carrier by boiling it with a 100 ml portion of 10% w nitric acid for 30 minutes (1 atm., i.e., 101.3 kPa) and determining in the combined extracts the relevant metals by using a known method, for example atomic absorption spectroscopy (See, for example, U.S. Pat. No. 5,801,259 and U.S. Patent Application Publication No. 2014/0100379 A1).

In one embodiment of the present invention, the porous body may have a silica content, as measured as $SiO_2$, of less than 0.2, preferably less than 0.1, weight percent, and a sodium content, as measured as $Na_2O$, of less than 0.2 weight percent, preferably less than 0.1, weight percent. In some embodiments, the porous body of the present invention may have an acid leachable sodium content of 40 ppm or less. In yet further embodiments of the present invention, the porous body comprises alumina crystallites having a platelet morphology in a content of less than 20 percent by volume. In some embodiments, alumina crystallites having a platelet morphology in a content of less than 10 percent by volume are present in the porous body of the present invention.

In addition to the above physical properties, the porous body of the present invention has a pore architecture that provides at least one of a tortuosity of 7 or less, a constriction of 4 or less and a permeability of 30 mdarcys or greater. A porous body that has the aforementioned pore architecture has enhanced fluid transport properties and high mechanical integrity. In some embodiments, and when used as a carrier for a silver-based epoxidation catalyst, a porous body having the aforementioned pore architecture can exhibit improved catalyst properties. Typically, the pore architecture of the porous body of the present invention has a tortuosity of 7 or less and/or a constriction of 4 or less.

In one embodiment of the present invention, the porous body has a pore architecture that provides a tortuosity of 7 or less. In another embodiment, the porous body of the present invention has a pore architecture that provides a tortuosity of 6 or less. In yet another embodiment, the porous body of the present invention has a pore architecture that provides a tortuosity of 5 or less. In a further embodiment, the porous body of the present invention has a pore architecture that provides a tortuosity of 3 or less. The lower limit of the tortuosity of the porous body of the present invention is 1 (theoretical limit). In some embodiments, the tortuosity can be any number bounded between 1 and 7.

In one embodiment of the present invention, the porous body has a pore architecture that provides a constriction of 4 or less. In another embodiment, the porous body of the present invention has a pore architecture that provides a constriction of 3 or less, or even 2 or less. The lower limit of the constriction of the porous body of the present invention is 1. In some embodiments, the constriction can be any number bounded between 1 and 4.

In yet another embodiment of the present invention, the porous body has 2-4 times improved effective gas diffusivity due to the combination of low tortuosity and high porosity.

In one embodiment, the porous body of the present invention has a pore architecture that provides a permeability of 30 mdarcys or greater. In another embodiment, the porous body of the present invention has a pore architecture that provides a permeability of 200 mdarcys or greater.

The porous bodies of the present invention can be prepared by first providing a precursor mixture comprising alpha alumina powders, non-silicate binder, burn-out materials, solvents, and lubricants. An example of a non-silicate binder is boehmite ($\gamma$-AlOOH). Typically, the non-silicate binder is dispersed into deionized water or another solvent. In the present invention, the alpha alumina powder that is used in the precursor mixture is a milled alpha alumina powder that has a particle size from 0.1 microns to 6 microns. All components of the porous body precursor mixture are homogenously mixed.

The principle burnout material that can be used in the present invention comprises any conventional burnout material having a particle size from 1 micron to 10 microns. Some examples of burnout materials that can be used as the principle burnout material include cellulose, substituted celluloses, e.g., methylcellulose, ethylcellulose, and carboxyethylcellulose, stearates (e.g., organic stearate esters, such as methyl or ethyl stearate), waxes, granulated polyolefins (e.g., polyethylene and polypropylene), walnut shell flour, and the like, which are decomposable at the firing temperatures used in preparation of the porous body. In one example, polyethylene having a particle size from 3 microns to 8 microns can be used as the principle burnout material. In another example, paraffin or PTFE having a particle size from 1 micron to 9 microns can be used as the principal burnout material.

In some embodiments, unmilled alpha alumina powder may be added to the precursor mixture. In other embodiments, the unmilled alpha alumina powder can be added to the precursor mixture mentioned above together with the milled alpha alumina powder. The unmilled alpha alumina powder that can be used in the present invention may have an average particle size in a range from 10 microns to 100 microns. When unmilled alpha alumina powder is employed, the weight ratio of milled alpha alumina powder to unmilled alpha alumina powder can be from about 0.25:1 to about 5:1.

An auxiliary burnout material can be optionally added to the precursor mixture. When employed, the auxiliary burnout material has a particle size that is greater than the particle size of the principle burnout material mentioned above. The auxiliary burnout material may be a same, or different, burnout material as the principle burnout material. In one example, graphite having a particle size from 3 microns to 10 microns can be used as the auxiliary burnout material. In another example, paraffin or PTFE having a particle size from 1 micron to 9 microns can be used as the auxiliary burnout material. When an auxiliary burnout material is used, the weight ratio of the principal burnout material to the auxiliary burnout material can be in a range from 1.1 to 5.4.

In the precursor mixture mentioned above, a conventional lubricant such as, for example, Petrolatum, can be used. The amount of lubricate that can be added at this point of the present invention may comprise the total amount of, or a partial amount, of the lubricate that used in forming the porous bodies of the present invention.

In some embodiments of the present invention, additional unmilled alpha alumina powder having a larger particle size than the previously mentioned unmilled alpha alumina powder may be added to the precursor mixture. When the additional unmilled alpha alumina powder is employed, the weight ratio of milled alpha alumina powder to additional unmilled alpha alumina powder can be from about 0.2:1 to about 5:1. In some embodiments, additional lubricate can be added to the precursor mixture.

The precursor mixture mentioned above is then formed to provide a desired shape of the porous body. The shape may vary and can be selected based upon the desired application of the resultant porous body that is eventually formed. Forming of the precursor mixture is typically performed by pressing, extrusion, molding, casting, etc. In one embodiment of the present invention, extruding may be performed using an extruder die that can produce hollow cylinder shapes which then can be cut to pieces of substantially equal length. The extrudate after cutting is then dried using any conventional drying means. Subsequently, the dried extrudate can be transferred into a furnace in order to remove the water and burn out most of the burnout materials and other fillers that may be present. Depending on the burnout material type, heat treatment can performed at temperatures from 100° C. to 1,000° C. with heating rates varying between 10° C./hr to 100° C./hr. Subsequently, the extrudate can be sintered. In one example, sintering may be performed in flowing air at a temperature from 1200° C. to 1600° C. After sintering, the resultant porous body is cooled to room temperature. The heating and cooling rates can be within a range from 1° C./min up to 5° C./min. Other heating and cooling rates within a range from 0.5° C./min up to 20° C./min can also be used in the present invention for providing the porous bodies.

In one embodiment, the porous body contains essentially only alumina, or alumina and boehmite components, in the absence of other metals or chemical compounds except that trace quantities of other metals or compounds may be present. A trace amount is an amount low enough that the trace species does not observably affect functioning or ability of a catalyst prepared thereupon.

In one embodiment of the present invention, the porous body described above can be used as a catalyst carrier (i.e., catalyst support) which includes one or more catalytically active materials, typically metals, disposed on and/or in the porous body. The one or more catalytically active materials can catalyze a specific reaction and are well known in the art. In some embodiments, the catalytically active material includes one or more transition metals from Groups 3-14 of the Periodic Table of Elements and/or Lanthanides. In such applications, one or more promoting species (i.e., species that aide in a specific reaction) can be also disposed on and/or in the porous body of the present invention. The one or more promoting species may be, for example, alkali metals, alkaline earth metals, transition metals, and/or an element from Groups 15-17 of the Periodic Table of Elements.

In another embodiment of the present invention, the porous body described above can also be used as a filter in which liquid or gas molecules can diffuse through the pores of the porous body described above. In such an application, the porous body can be placed along any portion of a liquid or gas stream flow. In yet another embodiment of the present invention, the porous body described above can be used as a membrane.

The porous body of the present application can be particularly useful as a carrier for a silver-based epoxidation catalyst. In such an embodiment, a catalytically effective amount of silver is disposed on and/or in the porous body. In one embodiment, the catalytic amount of silver is from 10% by weight to 50% by weight. The catalytic amount of silver may be achieved utilizing a single impregnation or multiple impregnations may be used, as described below, and calcinations, as also defined below.

The silver-based epoxidation catalyst can be prepared by impregnating the porous body described above with silver ions, compounds, complexes, and/or salts dissolved in a suitable solvent sufficient to cause deposition of silver precursor compound onto and/or into the porous body. In some embodiments of the present invention, and as will be described in greater detail herein below, the porous body described above can be simultaneously impregnated and incorporated with silver along with any additional desired promoter or additional promoter combination, by any of the conventional methods known in the art, e.g., by excess solution impregnation, incipient wetness impregnation, spray coating, and the like. Typically, the porous body described above is placed in contact with the silver-containing solution until a sufficient amount of the solution is absorbed by the porous body. Infusion of the silver-containing solution into the porous body can be aided by invention of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908, 343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for catalyst deposition by impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In one embodiment, the solution comprises an aqueous solution of silver oxalate and ethylene diamine. The complexing/solubilizing agent may be present in the impregnating solution in an amount from about 0.1 moles to about 10 moles of ethylene diamine per mole of silver, preferably from about 0.5 moles to about 5 moles, and more preferably from about 1 moles to about 4 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% by weight of silver to 45% by weight of silver, and even more typically, from about 5% by weight of silver to 35% by weight of silver.

In addition to silver, the silver-based epoxidation catalyst of the present invention may also include any one or more promoting species in a promoting amount. The one or more promoting species can be incorporated into the porous body described above either prior to, coincidentally with, or subsequent to the deposition of the silver. As used herein, a "promoting amount" of a certain component refers to an amount of that component that works effectively to provide an improvement in one or more of the catalytic properties of a subsequently formed catalyst when compared to a catalyst not containing the component.

For example, silver-based epoxidation catalysts may include a promoting amount of a Group 1 alkali metal or a mixture of two or more Group 1 alkali metals. Suitable Group 1 alkali metal promoters include, for example, lithium, sodium, potassium, cesium, rubidium, or combinations thereof. Thus, and in one example, a silver-based epoxidation catalyst including silver and one of lithium, sodium, potassium, cesium and rubidium can be provided in the present invention. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the additional alkali metal.

The silver-based epoxidation catalyst may also include a promoting amount of a Group 2 alkaline earth metal or a mixture of two or more Group 2 alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The silver-based epoxidation catalyst may also include a promoting amount of a main group element or a mixture of two or more main group elements. Suitable main group elements include any of the elements in Groups 13 (boron group) to 17 (halogen group) of the Periodic Table of the Elements. In one example, a promoting amount of one or more sulfur compounds, one or more phosphorus compounds, one or more boron compounds or combinations thereof can be used.

The silver-based epoxidation catalyst may also include a promoting amount of a transition metal or a mixture of two or more transition metals. Suitable transition metals can include, for example, the elements from Groups 3 (scandium group), 4 (titanium group), 5 (vanadium group), 6 (chromium group), 7 (manganese group), 8-10 (iron, cobalt, nickel groups), and 11 (copper group) of the Periodic Table of the Elements, as well as combinations thereof. More typically, the transition metal is an early transition metal selected from Groups 3, 4, 5, 6, or 7 of the Periodic Table of Elements, such as, for example, hafnium, yttrium, molybdenum, tungsten, rhenium, chromium, titanium, zirconium, vanadium, tantalum, niobium, or a combination thereof.

In one embodiment of the present invention, the silver-based epoxidation catalyst includes silver, cesium, and rhenium. In another embodiment of the present invention, the silver-based epoxidation catalyst includes silver, cesium, rhenium and one or more species selected from Li, K, W, Zn, Mo, Mn, and S.

The silver-based epoxidation catalyst may also include a promoting amount of a rare earth metal or a mixture of two or more rare earth metals. The rare earth metals include any of the elements having an atomic number of 57-71, yttrium (Y) and scandium (Sc). Some examples of these elements include lanthanum (La), cerium (Ce), and samarium (Sm).

The transition metal or rare earth metal promoters are typically present in the silver-based epoxidation catalyst in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of the aforementioned promoters, aside from the alkali metals, can be in any suitable form, including, for example, as zerovalent metals or higher valent metal ions.

After impregnation with silver, and any promoters, the impregnated porous alumina body is removed from the solution and calcined for a time sufficient to reduce the silver component to metallic silver and to remove volatile decomposition products from the silver-containing porous alumina body. The calcination is typically accomplished by heating the impregnated porous alumina body, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated carriers. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated porous alumina body carrier is typically exposed to a gas atmosphere comprising oxygen, such as air, or an inert gas, such as nitrogen, or both. The inert gas may also include a reducing agent as well known in the art.

The silver-based epoxidation catalyst mentioned above can be used in a method for the vapor phase production of ethylene oxide by conversion of ethylene to ethylene oxide in the presence of oxygen. Generally, the ethylene oxide production process is conducted by continuously contacting an oxygen-containing gas with ethylene in the presence of the above described silver-based epoxidation catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. A typical process for the oxidation of ethylene to ethylene oxide comprises the vapor phase oxidation of ethylene with molecular oxygen in the presence of the catalyst of the present invention in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with the silver-based epoxidation catalyst described above.

The silver-based epoxidation catalyst described above has been shown to be a particularly selective catalyst in the oxidation of ethylene with molecular oxygen to ethylene oxide. Selectivity values of at least about 83 mol % up to about 93 mol % are typically achieved. In some embodiments, the selectivity is from about 87 mol % to about 93 mole %. The conditions for carrying out such an oxidation reaction in the presence of the silver-based epoxidation catalyst described above broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or byproducts, unreacted materials are typically returned to the oxidation reactor.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide that is produced can be separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from about 0.3 to about 6, preferably from about 0.3 to about 2.0, volume percent.

In some embodiments of the present invention, the silver-based epoxidation catalyst described above exhibits enhanced catalytic activity, enhanced selectivity (at both the start and end of the run), enhanced heat transfer, and/or enhanced stability over equivalent prior art silver-based catalysts in which commercial carriers not having the pore architecture described above are used. Example 3 that follows illustrates that a silver-based epoxidation catalyst containing a porous body of the present invention exhibited enhanced performance as compared to an equivalent silver-based epoxidation catalyst that contains a customary alpha-alumina carrier.

Examples have been set forth below for the purpose of further illustrating the present invention. The scope of the present invention is not limited to the examples set forth herein. Other examples, such as porous filters, membranes, and other types of catalysts, are not discussed in more detail.

Example 1: Porous Bodies Preparation and Characterization

Typical compositions of the precursor mixtures of the porous bodies of the present invention are shown in Table 1. Porous bodies of the present invention were typically prepared under constant stirring by (i) dispersing binder in water; (ii) adding milled and/or unmilled alpha alumina powder; (iii) adding burn-out 1, if any; (iv) adding burn-out 2 if any; and (v) adding lubricant. Particular quantities and types of the individual constituents of each precursor mixture of the present invention are shown in Table 1. Subsequently, the mixture was extruded using 2" Bonnot extruder with a single die to produce extrudate in the shape of hollow cylinders. The extrudates were cut into equal-length pieces and then dried under a heat lamp for 1 hr. Subsequently, the cut and dried extrudates were moved to a furnace and subjected to the following heat treatments: (i) pyrolysis of the burn-out was performed in flowing air at 800° C. for 16 hrs with average heating rate of 23° C./hr; followed by (ii) sintering at 1250-1550° C. for 12 hrs with a heating and cooling rates of 2.0° C./min.

Porous bodies, PB1-PB7, which are representative of the present invention, were prepared utilizing the general method described above and the resultant porous bodies were characterized using the procedures mentioned above. PB8 is a reference carrier for silver-based epoxidation catalysts.

Table 2 provides a tabulation of the pore architecture-derived properties of the different porous bodies PB1-PB8, while Table 3 provides the measured physical properties of the various porous bodies, PB1-PB8. The measured impurities for PB1-PB7 are as follows: [$SiO_2$] from 0.02 to 1.0 weight percent, [$Na_2O$] from 0.01 to 0.10 weight percent and acid-leachable sodium of from 5 to 35 ppm. PB8 had the following impurities: [$SiO_2$]=4.5 weight percent, [$Na_2O$]=0.2 weight percent and acid-leachable sodium of about 100 ppm.

FIG. 1A shows the cumulative intrusion curves, while FIG. 1B shows the log differential intrusion curves, measured on PB1 and PB3 by Hg intrusion porosimetry. Although both types of curves are overlapping within the accuracy of the measurement, PB1 and PB3 have very different porous architectures and other properties, as shown in FIGS. 2A, 2B, 3A, and 3B, and in Table 2. PB1 consists of a smaller number of larger pores separated by thick walls, and has a high tortuosity and constriction than PB3. Conversely, PB3 consists of a larger number of smaller pores separated by thin walls, and has a lower tortuosity and constriction than PB1. The permeability for both PB1 and PB3 is comparable. Based on these measurements, PB3 has improved diffusive gas transport within a catalyst pellet (i.e., higher effective diffusivity) due to lower tortuosity and constriction values.

Figure 4A:
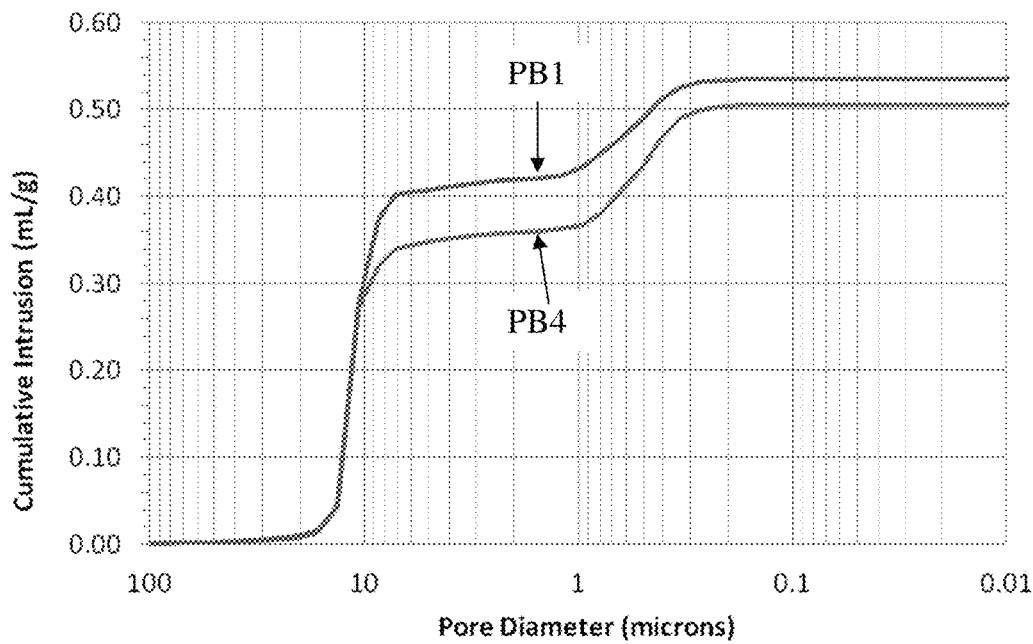
FIG. 4A shows the cumulative intrusion curves of PB1 and porous body 4 (PB4).
Figure 4B:
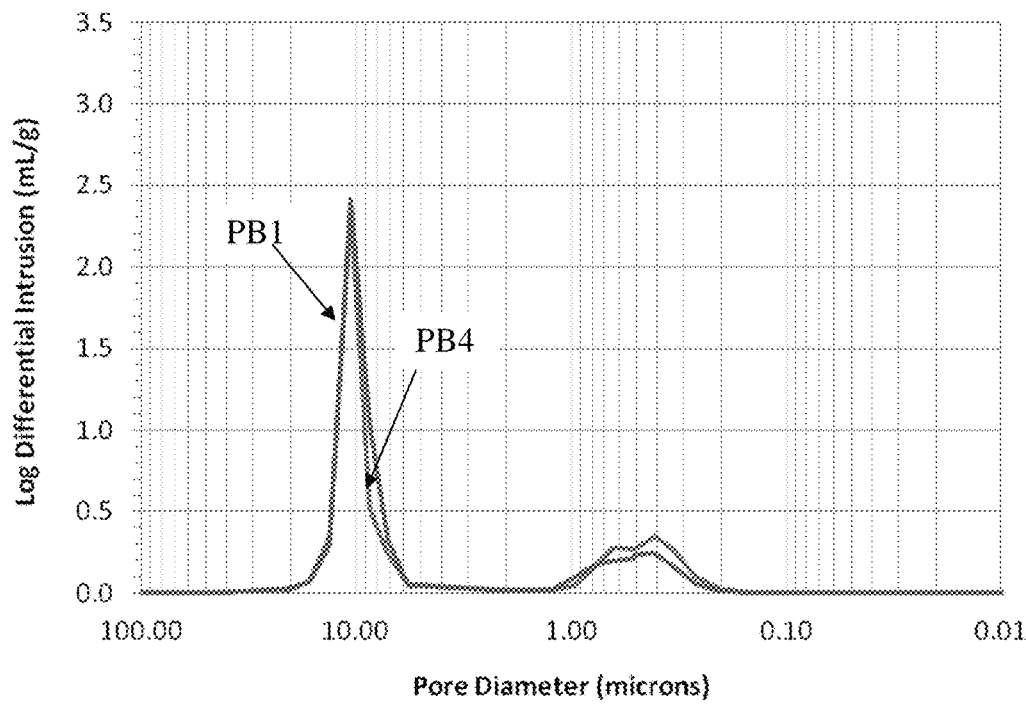
FIG. 4B shows the log differential intrusion curves of PB1 and PB4.
Figure 5A:
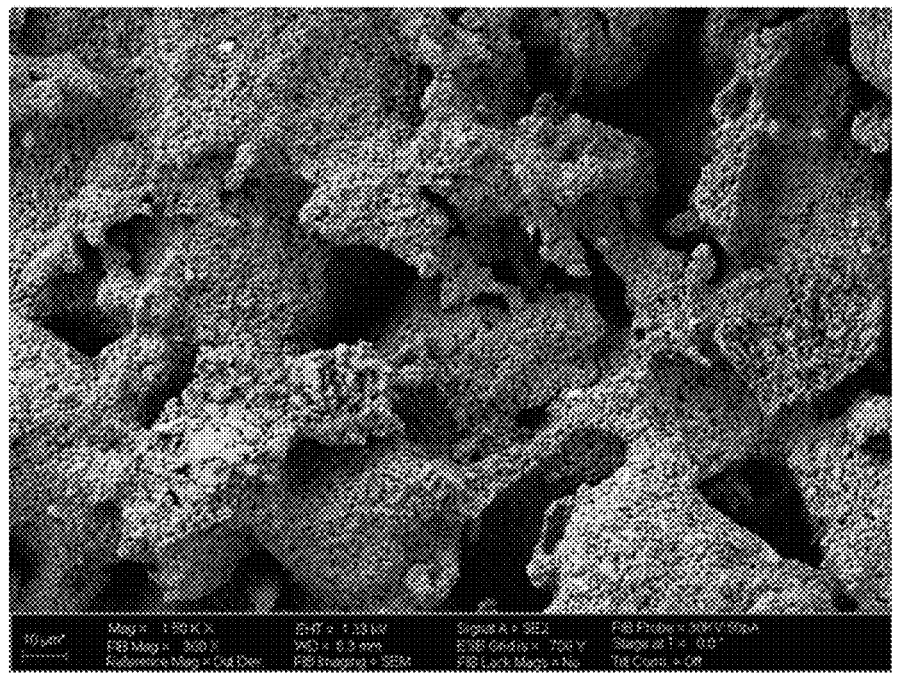
FIGS. 5A-5B are SEM images of PB4 at magnifications of 1500× (FIG. 5A) and 5000× (FIG. 5B).
Figure 5B:
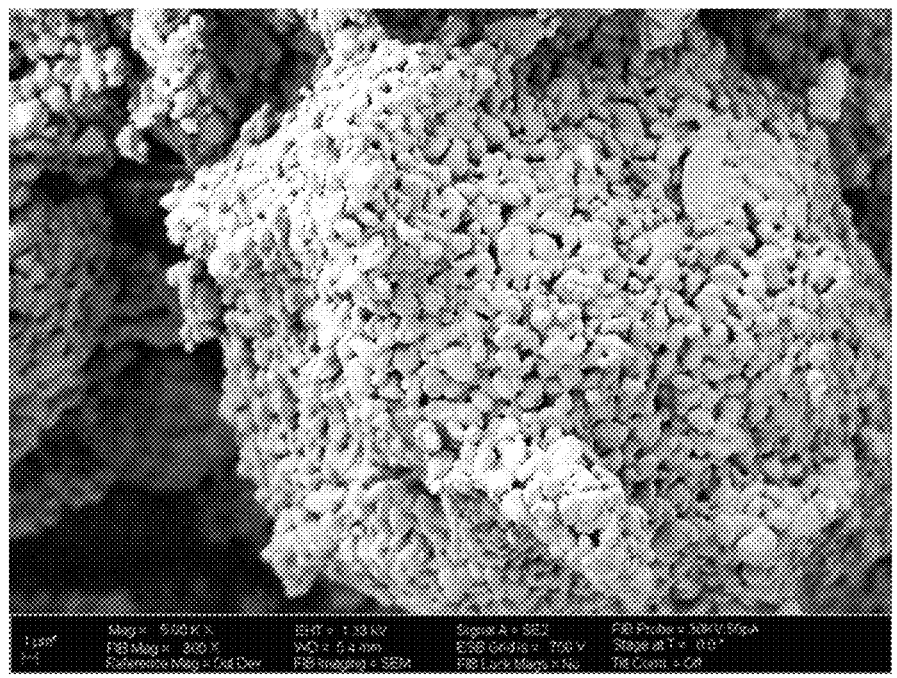

FIG. 4A shows the cumulative intrusion curves, while FIG. 4B shows the log differential intrusion curves, measured on PB1 and PB4 by Hg intrusion porosimetry. The log differential distribution curves are identical. The prior art teaches that they should represent the same porous architectures that results in particular performance. However, PB1 and PB4 have very different porous architectures and other properties, as shown in FIGS. 2A, 2B, 5A, and 5B, and in Table 2. PB1 consists of a smaller number of larger pores separated by thick walls, and has a higher tortuosity, constriction, and lower permeability than PB4. Conversely, PB4 consists of a very small number of very large pores separated by very thick walls, and has a lower tortuosity, constriction, and higher permeability than PB1. Based on these measurements, PB4 has improved diffusive gas transport within a catalyst pellet (i.e., higher effective diffusivity) due to lower tortuosity and constriction values. PB4 also has enhanced gas flow properties driven by pressure drop.

Figure 6A:
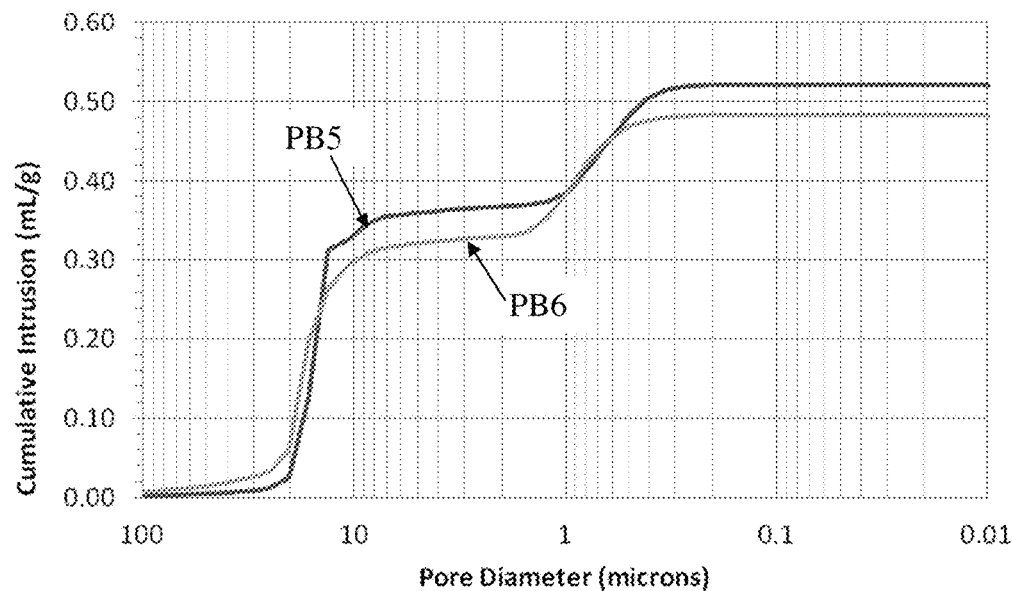
FIG. 6A shows the cumulative intrusion curves of porous body 5 (PB5) and porous body 6 (PB6).
Figure 6B:
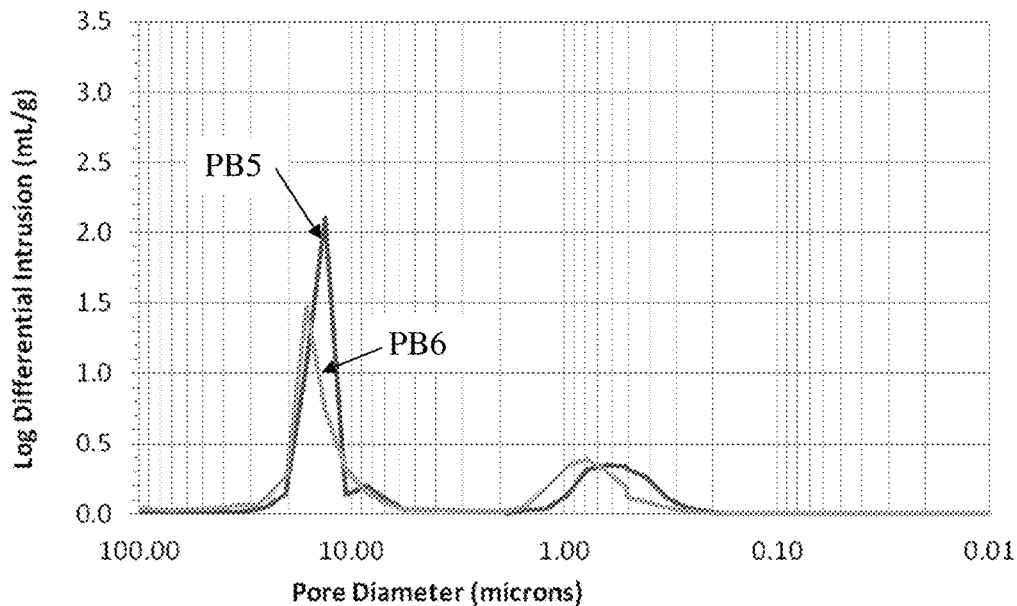
FIG. 6B shows the log differential intrusion curves of PB5 and PB6.
Figure 7A:
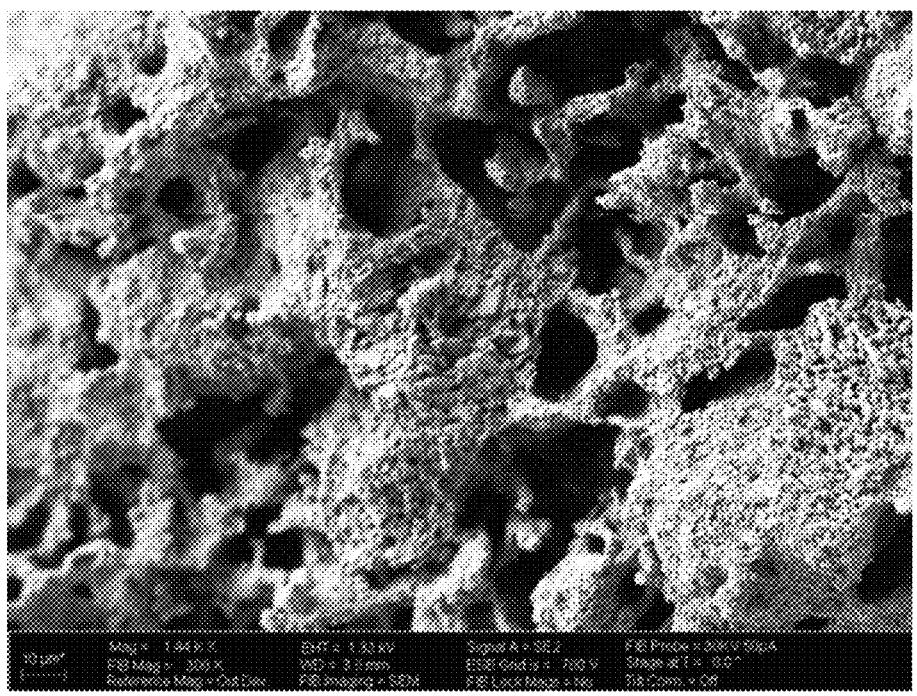
FIGS. 7A-7B are SEM images of PB5 at magnifications of 1500× (FIG. 7A) and 5000× (FIG. 7B).
Figure 7B:
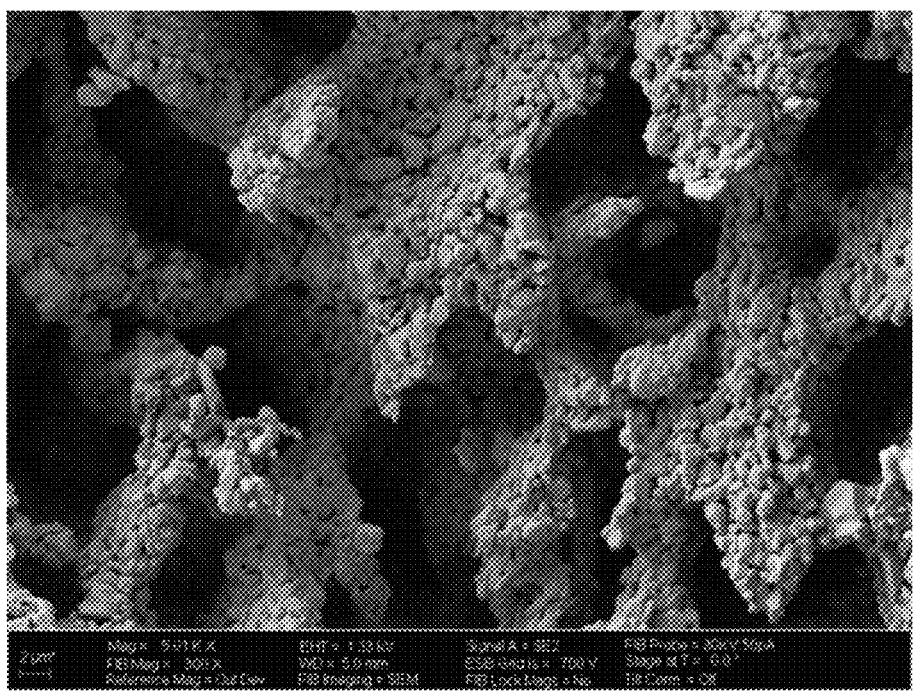
Figure 8A:
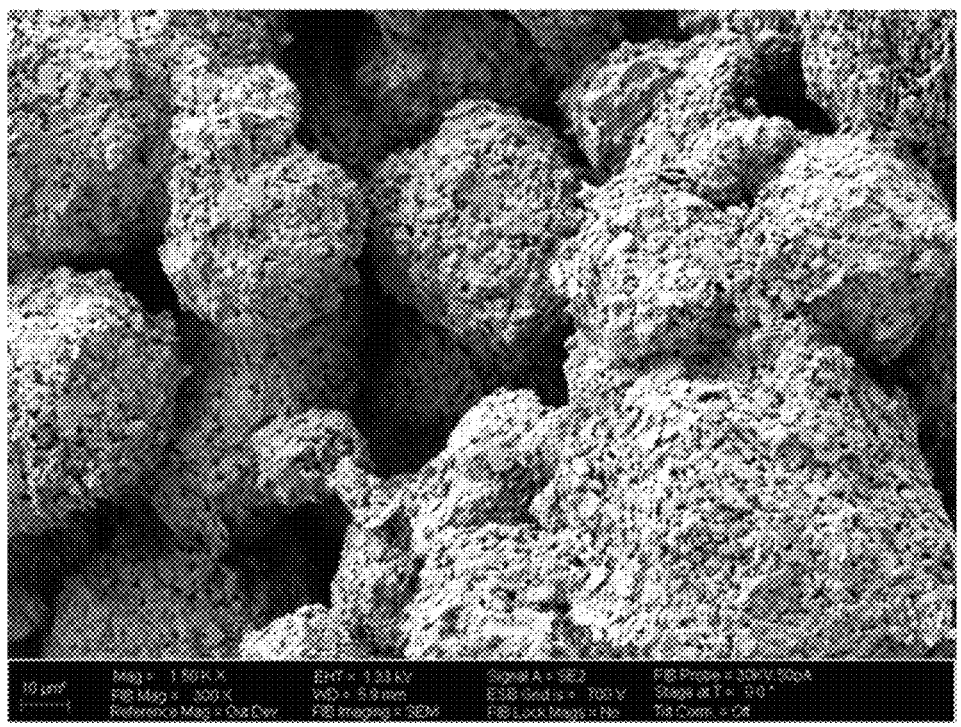
FIGS. 8A-8B are SEM images of PB6 at magnifications of 1500× (FIG. 8A) and 5000× (FIG. 8B).
Figure 8B:
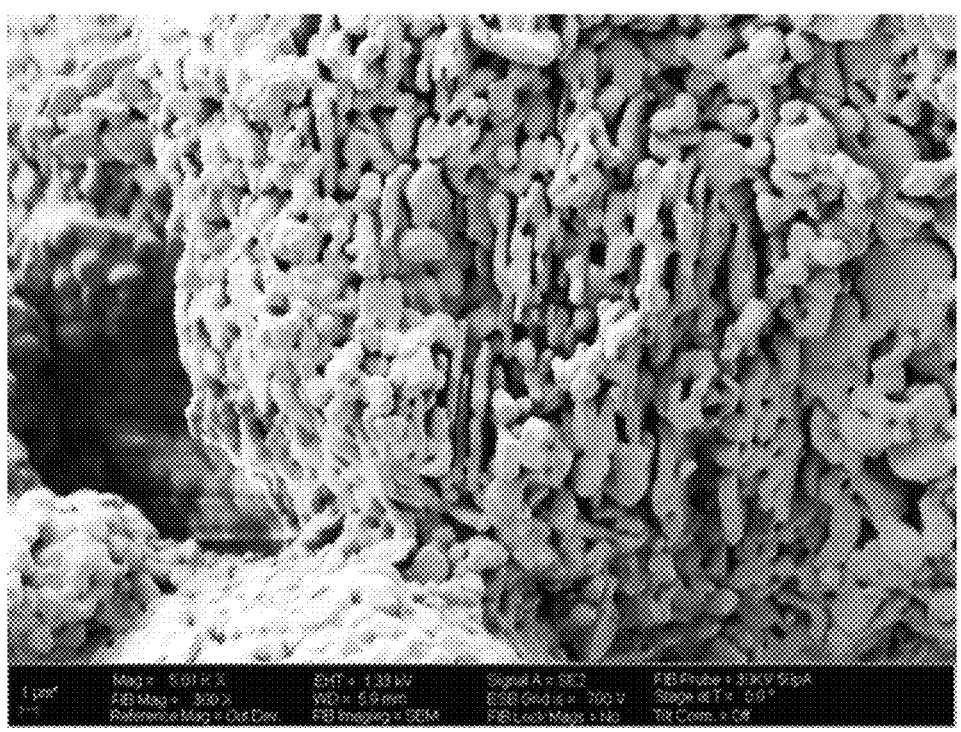

FIG. 6A shows the cumulative intrusion curves, while FIG. 6B shows the log differential intrusion curves, measured on PB5 and PB6 by Hg intrusion porosimetry. Both cumulative and log differential distribution curves are very similar, yet not perfectly overlapping. PB5 and PB6 have very different porous architectures and other properties, as shown in FIGS. 7A, 7B, 8A, and 8B, and in Table 2. PB5 consists of a smaller number of larger pores separated by thick walls, and has a lower tortuosity, and constriction than PB6. Conversely, PB6 consists of very large pores with no walls between them, and has a higher tortuosity and constriction than PB5. The permeability for both PB5 and PB6 are comparable. Based on these measurements, PB5 has improved diffusive gas transport within a catalyst pellet (i.e., higher effective diffusivity) due to lower tortuosity and constriction values.

TABLE 1

Ranges of compositions of porous body precursors

| Precursor for Porous Body No. | Unmilled Alpha Alumina Powder (g) | Milled Alpha Alumina Powder (g) | Binder (g) | Solvents and Lubricants Total (g) | Burn-out 1 (g) | Burn-out 2 (g) |
|---|---|---|---|---|---|---|
| PB1 (Inventive Example) | 250-500 | 500-700 | 100-300 | 500-700 | 250-500 | 0-200 |
| PB2 (Inventive Example) | 0-250 | 500-700 | 200-400 | 500-800 | 300-600 | 150-350 |
| PB3 (Inventive Example) | 200-450 | 500-700 | 150-350 | 600-950 | 350-650 | 100-300 |
| PB4 (Inventive Example) | 600-900 | 500-700 | 100-250 | 500-700 | 250-450 | — |
| PB5 (Inventive Example) | 500-700 | 700-900 | 100-250 | 500-700 | 250-450 | — |
| PB6 (Inventive Example) | 1,500 | — | 100-250 | 700-900 | — | — |
| PB7 (Inventive Example) | 0-150 | 500-700 | 150-350 | 500-700 | 350-550 | 100-300 |
| PB8 (Comparative Example) | Comparative Example PB8 was made using a different methodology, not of the present invention | | | | | |

TABLE 2

Comparison of properties of different porous bodies

| Porous Body No. | Microstructure (by SEM) | Tortuosity (—) | Constriction (—) | Permeability (mdarcy) | Effective Diffusivity normalized to PB8 |
|---|---|---|---|---|---|
| PB1 (Inventive Example) | Smaller number of larger pores separated by thick walls | 3.8 | 2.6 | 220 | 2.38 |
| PB2 (Inventive Example) | Larger number of smaller pores separated by thin walls | 3.3 | 2.3 | 88 | 2.88 |

TABLE 2-continued

Comparison of properties of different porous bodies

| Porous Body No. | Microstructure (by SEM) | Tortuosity (—) | Constriction (—) | Permeability (mdarcy) | Effective Diffusivity normalized to PB8 |
|---|---|---|---|---|---|
| PB3 (Inventive Example) | Larger number of smaller pores separated by thin walls | 3.1 | 2.2 | 241 | 3.04 |
| PB4 (Inventive Example) | Very small number of very large pores separated by very thick walls | 2.4 | 1.6 | 397 | 3.60 |
| PB5 (Inventive Example) | Smaller number of larger pores separated by thick walls | 2.5 | 1.7 | 678 | 3.49 |
| PB6 (Inventive Example) | Very large pores, no walls between them | 3.1 | 2.1 | 731 | 2.74 |
| PB7 (Inventive Example) | Larger number of smaller pores separated by thin walls | 4.3 | 3.0 | 37 | 2.21 |
| PB8 (Comparative Example) | N/A | 8.3 | 5.3 | 15 | 1.00 |

TABLE 3

Ranges of properties for different porous bodies

| Extrudate Composition No. | Water Absorption (%) | Pore Volume (mL/g) | Total Porosity (%) | BET Surface Area (m$^2$/g) | Average Crush Strength (N) |
|---|---|---|---|---|---|
| PB1 (Inventive Example) | 55-62 | 0.55-0.62 | 69-71 | 0.9-1.0 | 51-77 |
| PB2 (Inventive Example) | 66-84 | 0.66-0.84 | 73-77 | 0.6-1.2 | 37-60 |
| PB3 (Inventive Example) | 58-82 | 0.58-0.82 | 70-77 | 0.7-0.9 | 10-62 |
| PB4 (Inventive Example) | 49-53 | 0.49-0.53 | 66-68 | 0.9-1.2 | 46-60 |
| PB5 (Inventive Example) | 43-52 | 0.43-0.52 | 63-68 | 0.6-1.1 | 51-105 |
| PB6 (Inventive Example) | 35-45 | 0.35-0.45 | 58-64 | 0.7-0.8 | 43-74 |
| PB7 (Inventive Example) | 60-90 | 0.60-0.90 | 71-78 | 1.0-2.2 | 64-94 |
| PB8 (Comparative Example) | 35-55 | 0.35-0.55 | 58-69 | 0.4-1.0 | 50-80 |

Example 2: Preparation of Inventive Catalyst 1 and Comparative Catalyst 1

Silver Stock Solution for silver-based ethylene oxide catalysts: 277.5 g of deionized water was placed in cooling bath to maintain temperature during the whole preparation under 50° C. At continuous stirring, 221.9 g of ethylenediamine was added in small portions to avoid overheating. 174.1 g of oxalic acid dihydrate was then added to the water-ethylenediamine solution in small portions. After all oxalic acid was dissolved, 326.5 g of high purity silver oxide was added to solution in small portions. After all silver oxide was dissolved and the solution was cooled to about 35° C. it was removed from the cooling bath. After filtration, the solution contained roughly 30 wt % silver, and had a specific gravity of 1.55 g/mL.

In this example, porous body PB2 of the present invention was selected as a carrier for Inventive Catalyst 1, while porous body PB8 was selected as a carrier for Comparative Catalyst 1. Each of the aforementioned carriers were washed prior to introducing silver and the other promoters to the carrier.

Catalyst 1 Preparation: A 300 g portion of the PB2 was placed in a flask and evacuated to about 0.1 torr prior to impregnation. To the above silver solution were added aqueous solutions of promoters including cesium (Cs) as cesium hydroxide, rhenium (Re) as perrhenic acid, and at least one other alkali metal as hydroxide in sufficient concentrations to prepare a catalyst composition in which the Cs content in the final catalyst was from 0 ppm to 1800 ppm, the rhenium content in the final catalyst was from 0 ppm to 900 ppm, and the silver (Ag) content was between 10 and 30 percent by weight. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier.

Calcination of the wet catalyst was performed on a moving belt calciner. In this unit, the wet catalyst was transported on a stainless steel belt through a multi-zone furnace. All zones of the furnace were continuously purged with pre-heated, nitrogen and the temperature was increased gradually as the catalyst passed from one zone to the next. The heat supplied to the catalyst was radiated from the furnace walls and from the preheated nitrogen. In this example, the wet catalyst entered the furnace at ambient temperature. The temperature was then increased gradually to a maximum of about 450° C. as the catalyst passed through the heated zones. In the last (cooling) zone, the temperature of the now calcined catalyst was immediately lowered to less than 100° C. before it emerged into ambient atmosphere. The total residence time in the furnace was approximately 45 minutes.

Both impregnation and calcination steps mentioned above were performed for Inventive Catalyst 1 and Comparative Catalyst 1 either once or in series of double, triple, or multiple catalyst preparations.

Comparative Catalyst 1 was prepared and calcined in exactly the same fashion as Inventive Catalyst 1 except that PB8 was used as the carrier instead of PB2.

Catalyst compositions both on carrier PB2 and PB8 were optimized on each particular carrier to yield maximum performance, i.e. combination of highest selectivity and highest activity. Only optimized catalysts were compared in the epoxidation of ethylene to ethylene oxide.

Example 3: Use of Inventive Catalyst 1 and Comparative Catalyst 1 in the Epoxidation of Ethylene to Ethylene Oxide Inventive Catalyst 1 was used on stream for about 2,000 hours in a laboratory micro-reactor at ΔEO of 3.8 mol %, and at a work rate of 355 kg EO/m³ cat/h. The following feed composition was used: $[C_2H_4]$=30%, $[O_2]$=7%, $[CO_2]$=1%, and $N_2$ balance gas. Comparative Example 1 was used under exactly the same conditions as mentioned above for Inventive Catalyst 1.

Catalyst performance comparison between Inventive Catalyst 1 utilizing PB2 as a carrier and Comparative Catalyst 1 utilizing PB8 as a carrier for the epoxidation of ethylene is shown in Table 4. In terms of selectivity and catalyst stability, Inventive Catalyst 1 utilizing PB2 as a carrier exhibited improved performance. The higher selectivity and stability could be assigned to improved gas diffusivity caused by lower tortuosity and constriction of PB2 as compared to PB8 (See, Table 2). The improved performance could be also assigned to higher purity of PB2 than PB8. Thus the combination of enhanced transport properties (i.e., lower tortuosity and constriction and higher effective diffusivity) with the higher purity of the inventive porous body of the present invention could be of great important in epoxidation of ethylene.

TABLE 4

Performances of EO catalysts on selected porous ceramics used as supports

| EO Catalyst No. | Porous Ceramics No. | Start of Run Selectivity | Start of Run Activity | End of Run Selectivity | End of Run Activity |
|---|---|---|---|---|---|
| Inventive Catalyst 1 | PB2 (Inventive Example) | 90% | 250° C. | 90% | 260° C. |
| Comparative Catalyst 1 | PB8 (Comparative example) | 88.5% | 247° C. | 87.5% | 257° C. |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A precursor mixture for producing a porous body, the precursor mixture comprising:
   (i) at least one milled alpha alumina powder having a particle size of 0.1 microns to 6 microns,
   (ii) a non-silicate binder, and
   (iii) at least one principle burnout material having a particle size of 1 micron to 10 microns.

2. The precursor mixture of claim 1, wherein the least one milled alpha alumina powder, the non-silicate binder, and the at least one principle burnout material are in a homogeneous mixture.

3. The precursor mixture of claim 1, wherein the at least one principle burnout material is a granulated polyolefin.

4. The precursor mixture of claim 3, wherein the granulated polyolefin is one of polyethylene and polypropylene.

5. The precursor mixture of claim 1, further comprising unmilled alpha alumina powder.

6. The precursor mixture of claim 5, wherein the unmilled alpha alumina powder has an average particle size from 10 microns to 100 microns.

7. The precursor mixture of claim 5, wherein a weight ratio of the milled alpha alumina powder to the unmilled alpha alumina powder is from about 0.25:1 to 5:1.

8. The precursor mixture of claim 5, further comprising an additional unmilled alpha alumina powder having a particle size greater than a particle size of the unmilled alpha alumina powder.

9. The precursor mixture of claim 8, wherein a weight ratio of the milled alpha alumina powder to the additional unmilled alpha alumina powder is from about 0.2:1 to 5:1.

10. The precursor mixture of claim 1, further comprising a solvent.

11. The precursor mixture of claim 1, wherein the least one milled alpha alumina powder is dispersed in deionized water.

12. The precursor mixture of claim 1, further comprising an auxiliary burnout material.

13. The precursor mixture of claim 12, wherein the auxiliary burnout material is graphite.

14. The precursor mixture of claim 12, wherein a weight ratio of the principle burnout material to the auxiliary burnout material is 1:1 to 5:4.

* * * * *